United States Patent [19]

Martin et al.

[11] 4,301,292
[45] Nov. 17, 1981

[54] 1-[2-(4,5-DIHYDRO-4,4-DIALKYL-2-OXAZOLYL)PHENYL]-4-(DIALKYLAMINO)-CYCLOHEXANOL

[75] Inventors: Lawrence L. Martin, Lebanon, N.J.; Manfred Worm, Wiesbaden-Naurod, Fed. Rep. of Germany

[73] Assignee: Hoechst-Roussel Pharmaceuticals, Incorporated, Somerville, N.J.

[21] Appl. No.: 211,150

[22] Filed: Nov. 28, 1980

Related U.S. Application Data

[62] Division of Ser. No. 73,055, Sep. 6, 1979.

[51] Int. Cl.$^3$ ............................................. C07D 263/08
[52] U.S. Cl. ............................................................. 548/239
[58] Field of Search .......................................... 548/239

[56] References Cited

U.S. PATENT DOCUMENTS 3,959,475  5/1976  Bauer et al. .................... 260/293.58
3,962,259  6/1976  Bauer et al. .................... 260/293.58
4,263,317  4/1981  Martin et al. ....................... 424/278

OTHER PUBLICATIONS

Martin L., Journal of Medicinal Chem., vol. 22, No. 11, pp. 1347–1354, (1979).
Klioze, S. and Bauer, Journal of Medicinal Chem., vol. 20, No. 4, pp. 610–612, (1977).
Allen, R. et al., Journal of Medicinal Chem., vol. 21, No. 11, pp. 1149–1154, (1978).

Primary Examiner—Donald G. Daus
Assistant Examiner—Sharon A. Gibson
Attorney, Agent, or Firm—Raymond R. Wittekind

[57] ABSTRACT

1-[2-(4,5-dihydro-4,4-dialkyl-2-oxazolyl)phenyl]-4-(dialkylamino)cyclohexanol as an intermedate for Spiro cyclohexane-1,1'(3'H)-isobenzofuran)s, which in turn are useful as antidepressants, tranquilizers, analgesics, and anticonvulsants.

2 Claims, No Drawings

1-[2-(4,5-DIHYDRO-4,4-DIALKYL-2-OXAZOLYL)-PHENYL]-4-(DIALKYLAMINO)CYCLOHEXANOL

This is a division of application Ser. No. 073,055 filed Sept. 6, 1979.

DESCRIPTION OF THE INVENTION

The present invention relates to novel spiro[cyclohexane-1,1'(3'H)-isobenzofuran]s of the formula

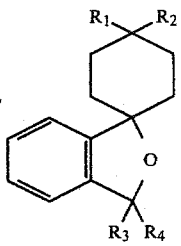

wherein $R_1$ is hydrogen; $R_2$ is $NR_5R_6$ wherein $R_5$ is hydrogen, loweralkyl;

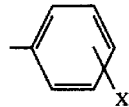, 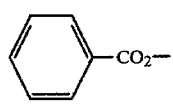

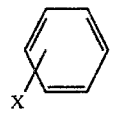

$R_6$ is hydrogen or loweralkyl; $R_3$ is hydrogen, loweralkyl or cycloalkyl having 3 to 7 carbon atoms, inclusive,

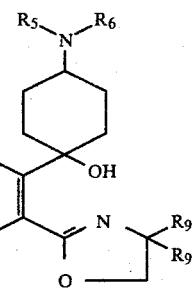

wherein X is hydrogen, halogen or loweralkyl; $R_4$ is hydrogen, loweralkyl or hydroxy; $R_3$ and $R_4$ taken together with the carbon atom to which they are attached form a carbonyl group; the geometrical isomers and optical antipodes thereof and the pharmaceutically acceptable salts thereof wherein $R_5$ is not the

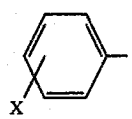

group, which compounds exhibit antidepressant, tranquilizer, analgesic and anticonvulsant activity.

Preferred isobenzofurans of the present invention are those wherein $R_3$ is and $R_4$ is hydrogen. Particularly preferred compounds are those wherein $R_2$ is $NR_5R_6$ wherein $R_5$ and $R_6$ are each independently hydrogen or loweralkyl and those wherein $R_6$ is hydrogen or loweralkyl and $R_5$ is

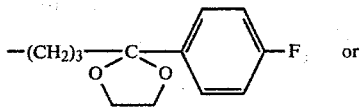 or

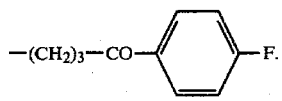

The present invention also relates to compounds of the formulas

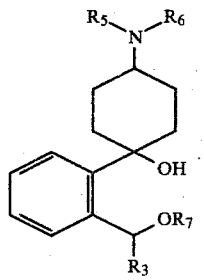

wherein $R_5$, $R_6$ and $R_9$ are loweralkyl; and the geometric isomers and optical antipodes thereof Ib wherein $R_3$ is loweralkyl or wherein X is hydrogen, halogen or loweralkyl; $R_5$, $R_6$ and $R_7$ are loweralkyl; and the geometrical isomers and optical antipodes thereof, which compounds are useful as intermediates for the preparation of isobenzofurans of Formula I.

As used throughout the specification and appended claims, the term "alkyl" denotes a straight or branched saturated hydrocarbon radical. Examples of alkyl groups are methyl, ethyl, isopropyl, butyl, pentyl and so forth. The term "cycloalkyl" denotes a saturated hydrocarbon group possessing at least one carbocyclic ring and having from 3 to 7 carbon atoms in the ring. Examples of cycloalkyl groups are cyclopropyl, cyclobutyl, cyclopentyl, cyclohexyl, cycloheptyl and the like. The term "alkanol" denotes a compound derived by coupling an alkyl group and hydroxyl radical. The term "lower" refers to the numerical range of 1 to 6.

In the formulas presented herein, substituents attached to the cyclohexane ring system may be in either the cis- or trans-configuration, i.e., the substituents may be, respectively, on the same side or on opposite sides of the average plane of the six-member ring. For example, the substituent $R_2$ attached to the 4-position of the cyclohexane ring may be in either the cis- or trans- configuration with respect to the spatial configuration of the C-1 ether bond. The geometrical isomerism of the compounds of the present invention is shown graphically in the reaction schemes. For example, the compound of formula V (Reaction Scheme A) exists in the cis-configuration, i.e., the $NR_5R_6$ and ether substituents being above the average plane of the cyclohexane ring as illustrated by the heavy lines (━━) and the corresponding compound of formula XXXVI (Reaction Scheme D) exists in the trans-configuration, i.e., the $NR_5R_6$ substituent being below the average plane of the cyclohexane ring as illustrated by the broken line (- - - -) and the ether substituted being above the average plane of the ring. A light line (—) indicates the substituent may be either above or below the average plane of the cyclohexane ring.

The isobenzofurans of the present invention lack an element of symmetry and exist as optical antipodes and in the racemic forms thereof. Optically active isobenzofurans may be prepared from optically active precursors. When optically inactive precursors are employed, optically active isobenzofurans may be prepared by standard resolution techniques well-known in the art utilizing optically active acids such as, for example, d-camphor-sulfonic acid and 1-tartaric acid.

The novel spiro[cyclohexane-1,1'(3'H)-isobenzofuran]s of the present invention and the intermediates thereto are prepared by the sequence of reactions depicted in Reactions Schemes A to D. To prepare spiro[cyclohexane-1,1'(3'H)-isobenzofuran]s of the cis-series, for example, a 2-bromobenzhydrylloweralkylether of formula II($R_7$ is loweralkyl), the synthesis of which is described by V. J. Bauer, et al., in J. Med. Chem., 19, 1315 (1976), is converted to its lithio derivative and condensed with a 4-diloweralkylaminocyclohexanone of formula III ($R_5$ and $R_6$ are loweralkyl) to form the cyclohexanol of formula IV ($R_5$, $R_6$ and $R_7$ are loweralkyl) which is cyclized to the cis-isobenzofuran V ($R_5$ and $R_6$ are loweralkyl) as illustrated in Reaction Scheme A.

The lithio derivative is formed by treating the bromo compound II dissolved or suspended in an ethereal solvent such as diethylether, dimethoxyethane, dioxane, tetrahydrofuran or the like, with a loweralkyllithium such as methyllithium, ethyllithium, n-butyllithium or the like in an inert hydrocarbon solvent such as pentane, hexane, heptane or the like. n-Butyllithium in hexane is preferred as is tetrahydrofuran as the ethereal solvent.

The condensation is conveniently carried out without isolation of the preformed lithio derivative at an initial reaction temperature of about $-20°$ to $-70°$ C., a range of about $-40°$ to $-50°$ C. being preferred, and a final reaction temperature of about $-90°$ to $20°$ C., a range of about $-70°$ to $0°$ C. being preferred.

The cyclization is accomplished by means of a mineral or organic acid. Suitable mineral acids include hydrochloric acid, hydrobromic acid, sulfuric acid and the like. Suitable organic acids include trifluoroacetic acid, methanesulfonic acid, para-toluenesulfonic acid and the like. Mineral acids are preferred. Hydrochloric acid is most preferred. The reaction may be preformed in a diluent such as acetic acid, or an inert solvent such as benzene or toluene when an organic acid is employed.

The subsequent modification of the diloweralkylamino substitutent of the isobenzofuran V is affected by dealkylation of the tertiary amino group of V to the secondary amino substituted derivative VIII ($R_6$ is loweralkyl) followed by alkylation to the fluorobenzoylpropyl compound X ($R_6$ is loweralkyl). The dealkylation is carried out in 2 steps by methods well known in the art. In the first step, V is treated with a loweralkylhaloorthoformate or phenylhaloorthoformate of formula VI ($R_8$ is loweralkyl or phenyl and Hal is halogen) in a halocarbon solvent such as dichloromethane, chloroform or the like, in the presence or absence of an acid scavenger to form the carbamate VII ($R_8$ is loweralkyl or phenyl and $R_6$ is loweralkyl). Suitable acid scavengers include alkali metal carbonates and bicarbonates, for example, sodoium bicarbonate, potassium carbonate and the like.

In the second step, the resulting carbamate VII is hydrolyzed by an alkali metal hydroxide such as lithium, sodium or potassium hydroxide, in a loweralkanol solvent such as methanol, ethanol or propanol at elevated temperatures, preferably at the reflux temperature of the reaction mixture.

The alkylation is accomplished by treating the secondary amine VIII with a 4-halo-p-fluorobutyrophenone of formula IX (Hal is halogen) or the ethylene ketal derivative thereof in polar aprotic solvent in the presence of an acid scavenger. Among suitable polar aprotic solvents there may be mentioned dimethylacetamide, dimethylformamide, hexamethylphosphoramide and the like. Among suitable acid scavengers there may be mentioned alkali metal carbonates and bicarbonates such as sodium and potassium carbonate and sodium and potassium bicarbonate. A reaction medium comprising sodium bicarbonate or potassium carbonate in dimethylformamide is preferred. While the reaction temperature is not narrowly critical, it is preferred to carry out the alkylation at a temperature within the range of about $60°-120°$ C., a temperature of about $90°$ C. being most preferred.

To promote the alkylation, particularly when a chloride is employed as the alkylating agent, it is desirable to use a promoter such as an alkali metal iodide. Lithium, sodium or potassium iodide may be employed. Potassium iodide is preferred.

When the ethylene ketal of IX is used as the alkylating agent, the ethylene ketal of X is obtained. To convert the cyclic ketal to the carbonyl group, X is hydrolyzed under aqueous acidic conditions, known per se. Appropriate conditions comprise mineral acids, for example, hydrochloric acid, cosolvents, for example, methanol or ethanol and an elevated reaction temperature, for example, the reflux temperature of the reaction medium.

The isobenzofuran V also serves as a precursor for the synthesis of 3'-loweralkyl substituted compounds of formula XIII ($R_4$, $R_5$ and $R_6$ are loweralkyl). To introduce the 3'-loweralkyl substituent, V is converted to its 3'-lithio derivative by the process used for the preparation of the lithio derivative of II. The lithio derivative so obtained is then alkylated with a loweralkyl halide of formula XI ($R_4$ is loweralkyl) or diloweralkylsulfate of formula XII ($R_4$ is loweralkyl). The alkylation proceeds conveniently in an ethereal solvent such as diethylether, dimethoxyethane, dioxane, tetrahydrofuran or the like. Tetrahydrofuran is preferred. The reaction temperature is not narrowly critical. However, it is preferred to perform the alkylation at a reduced temperature within the range of about $-80°$ to $0°$ C., a reduced temperature of about $-50°$ C. being most preferred.

Spiro[cyclohexane-1,1'(3'H)-isobenzofuran]s of the cis-series are also prepared, as illustrated in Reaction Scheme B, starting from a 2-(2-bromophenyl)-4,4-diloweralkyloxazoline of formula XIV ($R_9$ is loweralkyl), the synthesis of which is reported by V. J. Bauer, et al., in J. Med. Chem., 19, 1315 (1976). In this sequence, the lithio derivative of the bromophenyloxazoline XIV is formed and condensed with a diloweralkylcyclohexanone of formula III ($R_5$ and $R_6$ are loweralkyl) by processes substantially similar to those used for the formation of the lithio derivatives of bromodiphenylmethane II and the condensation of II to the isobenzofuran V via ether IV to afford the cyclohexanol XV ($R_5$, $R_6$ and $R_9$ are loweralkyl), which is cleaved with concomitant cyclization to the isobenzofuran-3-one XVI ($R_5$ and $R_6$ are loweralkyl).

The cleavage of the masked carboxylic acid group of XV, i.e., the oxazoline moiety, is conveniently accomplished by methods known in the art. For example, aqueous acids such as hydrobromic acid, hydrochloric acid and the like may be employed. Hydrochloric acid is preferred. The cleavage proceeds readily at the reflux temperature of the reaction mixture, although lower temperatures may also be employed to affect lactone formation.

Continuing the sequence, the isobenzofuran-3-one XVI is condensed with an organometallic reagent of the formula XVII (M is Li or MgHal wherein Hal is chloride, bromide or iodide and X is hydrogen, halogen or loweralkyl) to form the isobenzofuranol of formula XVIII ($R_5$ and $R_6$ are loweralkyl and X is as above) which is reductively cleaved to the diol XIX ($R_5$, $R_6$ and X are as above) and cyclized to the isobenzofuran XX ($R_5$ and $R_6$ are as above). The organometallic condensation is performed by art known methods employing, for example, reagents such as phenyllithium in hydrocarbon or ethereal solvents or mixtures thereof, at reduced temperatures within the range of about $-50°$ to $-10°$ C. or tolyl- or halophenylmagnesium bromides in ethereal solvents at a slightly elevated temperature near the reflux temperature of the reaction medium.

The reductive cleavage is also performed by art known methods using, for example, an alkali metal aluminum hydride such as lithium aluminum hydride, in an ethereal solvent such as tetrahydrofuran at a moderate temperature of about $40°$-$80°$ C.

The cyclization of XIX to XX is accomplished by methods known per se involving treatment with mineral acids such as, for example, hydrobromic or hydrochloric acid. A cosolvent such as acetic acid may be used to facilitate the reaction.

Alternatively, the isobenzofuranol XVIII is converted directly to the isobenzofuran XX by means of acidic reducing agents such as formic acid.

The isobenzofuran-3'-one XVI is also condensed with a loweralkylorganometallic of formula XXI ($R_3$ is loweralkyl and M is Li or MgHal wherein Hal is chloride, bromide or iodide) to yield the isobenzofuranol XXII ($R_3$, $R_5$ and $R_6$ are loweralkyl) which is reductively cleaved to the diol XXIII ($R_3$, $R_5$ and $R_6$ are as above) and cyclized to the isobenzofuran XXIV ($R_3$, $R_5$ and $R_6$ are as above). This sequence is carried out by processes substantially similar to those employed for the transformation of XVI to XX via XVIII and XIX.

The isobenzofuran-3'-one XVI is reduced to the 3'-unsubstituted isobenzofuran XXV ($R_5$ and $R_6$ are loweralkyl) by means of diborane in an ethereal solvent such as tetrahydrofuran at moderate temperatures up to the reflux temperature of the reaction medium.

By employing processes analogous to those used for the conversion of V to X and V to XIII (Reaction Scheme A), various N- and 3'-substituted isobenzofurans may be prepared from XX, XXIV and XXV.

In another aspect of the invention, illustrated in Reaction Scheme C, the lithio derivative of a 2-bromobenzhydryl loweralkyl ether of formula II is prepared as hereinbeforedescribed and is condensed with 1,4'-dioxaspiro[4.5]decan-8-one (XXVI) by a process analogous to that utilized for the conversion of II to V (Reaction Scheme A) to afford the isobenzofuran XXVII, the ethylene ketal protecting group of which is cleaved by art recognized means such as hydrochloric acid in methanol at room temperature to afford the cyclohexanone XXVIII. Utilizing the cyclohexanone XXVIII so obtained, the aminioisobenzofuran XXX is prepared by metal hydride reduction of the oxime derivative XXIX, both oxime formation and metal hydride reduction being accomplished by conventional methods, the latter involving the use of lithium aluminum hydride in tetrahydrofuran at elevated reaction temperatures.

Similarly, the methoxiiminoisobenzofuran XXXI is prepared by conventional methods and is reduced to the 3'-cyclohexyl-4-aminosiobenzofuran XXXII by hydrogen in the presence of a hydrogenation catalyst such as platinum, palladium, rubidium, ruthenium or the like, free or absorped on a solid support such as carbon, silica and the like, at from about 1 to about 10 atmospheres pressure.

Acetic acid is generally used as the hydrogenation solvent, although other solvents, for example, alkanols such as methanol, ethanol and the like are also applicable. In acetic acid, the hydrogenation progresses at a satisfactory rate at room temperature. Increased reaction temperatures may be employed with other solvents.

As depicted in Reaction Scheme D, to gain entry into the spiro[cyclohexane-1,1'(3'H)-isobenzofuran]s of the trans-series, benzanilide (XXXIII) is condensed with III to afford a mixture of cis-isobenzofuran-3-one XVI (Reaction scheme B) and the corresponding trans-isomer XXXIV ($R_5$ and $R_6$ are loweralkyl) which is separated into its component isomers. The trans-isobenzofuran XXXIV is carried through the sequence XXXV to XL by employing procedures hereinbefore described in Reaction Schemes A and B to obtain the desired N- and 3-substituted products.

The condensation is accomplished in a manner analogous to the conversion of II to IV (Reaction Scheme A), XIV to XV (Reaction Scheme B) and II to XXVII (Reaction Scheme C) by forming the dilithio derivative of benzanilide (XXXIII) and coupling it with cyclohexanone III.

The separation is readily accomplished by fraction crystallization of hydrohalide salt, such as the hydrobromide or hydrochloride, of the mixture of basic isomers from an appropriate solvent such as methanol and 2-propanol.

REACTION SCHEME A
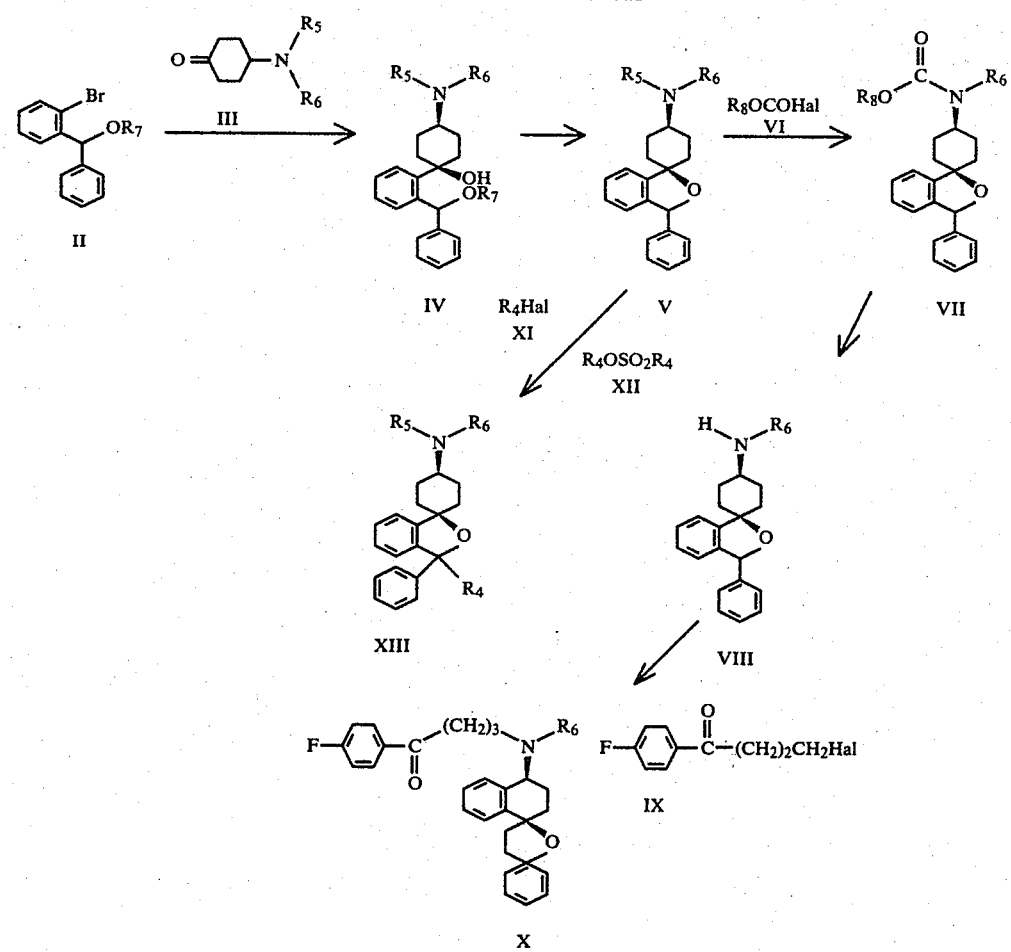
REACTION SCHEME B
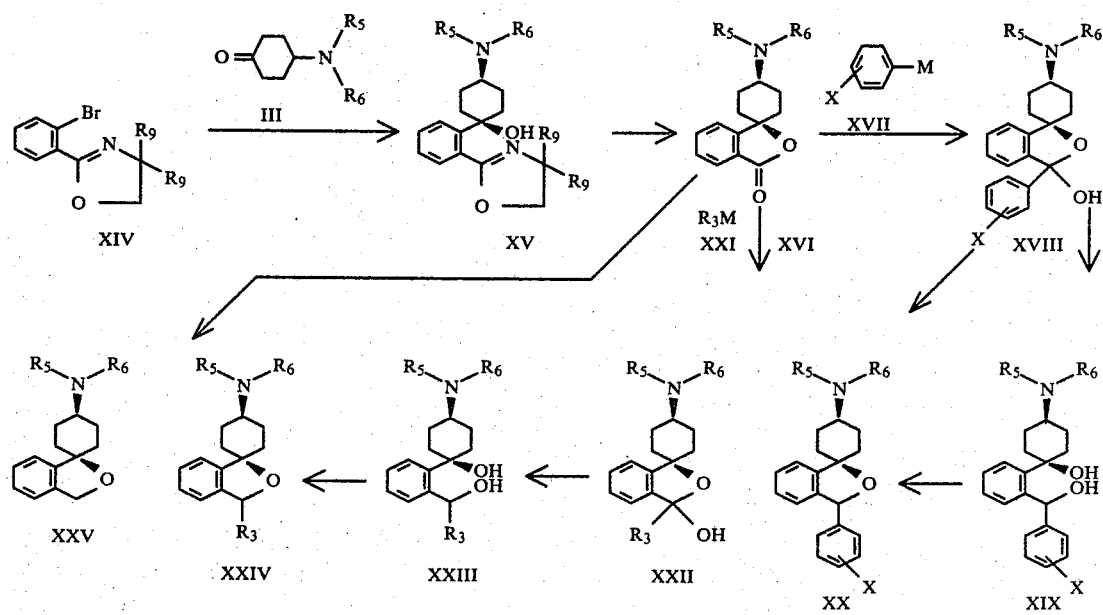

REACTION SCHEME C

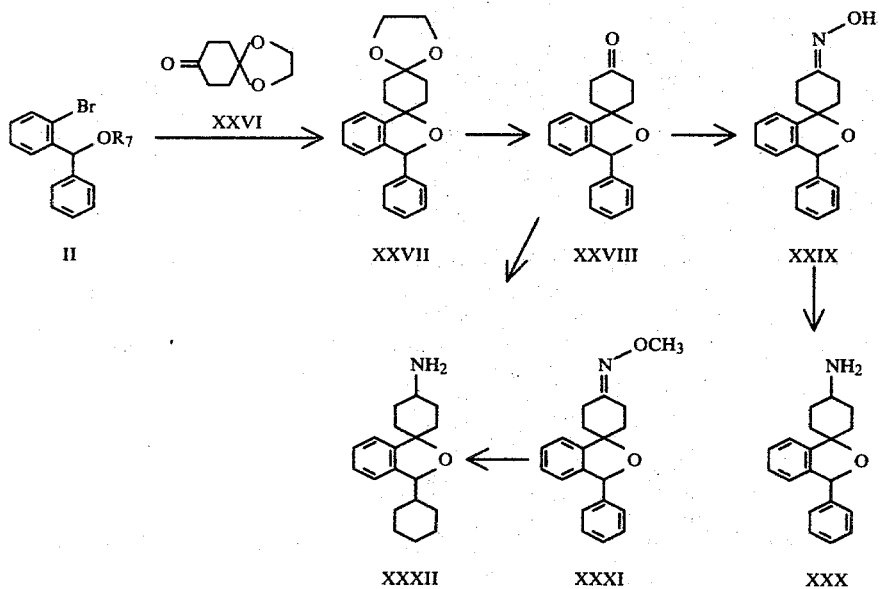

REACTION SCHEME D

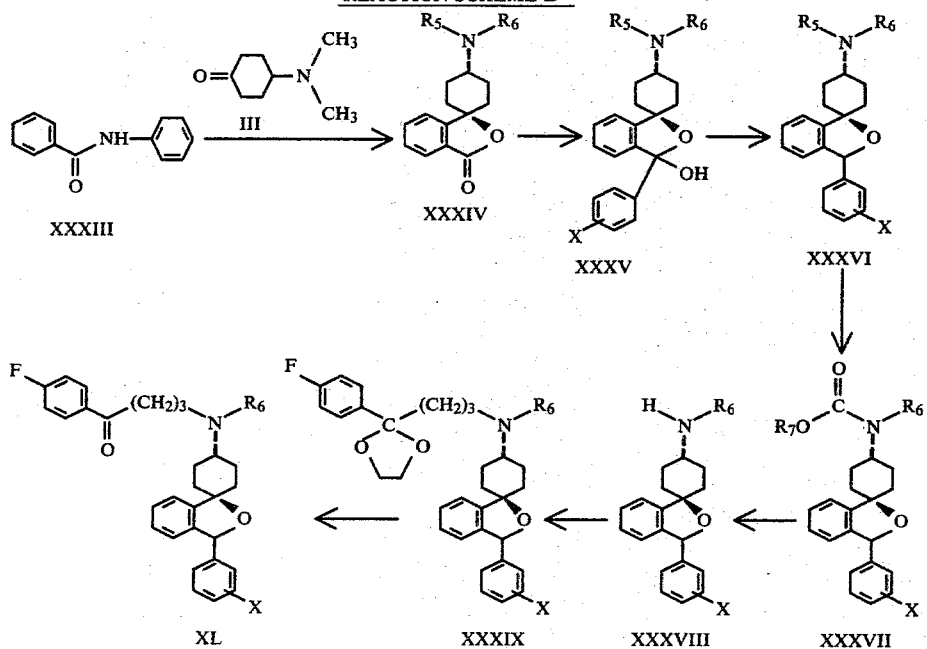

The utility of the compounds of the present invention in the treatment of depression in mammals is demonstrated by their ability to inhibit tetrabenazine induced depression in mice [International Journal of Neuropharmacology, 8, 73 (1969)], a standard assay for useful antidepressant properties. Thus, for instance, an intraperitoneal dose of 3.7 mg/kg of body weight and an oral dose of 9.4 mg/kg of body weight of cis-4-dimethylamino-3'-phenylspiro[cyclohexane-1,1'(3'H)-isobenzofuran] demonstrate a 50% inhibition of ptosis of tetrabenazine-induced depression in mice. Also, an oral dose of 8.4 mg/kg of body weight of cis-4-dimethylamino-3'-(4-fluorophenyl)spiro[cyclohexane-1,1'(3'H)-isobenzofuran] and an intraperitoneal dose of 2.0 mg/kg of body weight of 4-methylamino-3'-phenylspiro[cyclohexane-1,1'(3'H)-isobenzofuran]hydrochloride demonstrate a similar inhibition in this assay. These data indicate that the compounds of the present invention would be useful as antidepressants in mammals when administered in amounts ranging from 0.01 to 100 mg/kg of body weight per day.

Compounds of the present invention are also useful as anticonvulsant agents for mammals, as determined by Woodbury, L. A. and Davenport, V. D. [Arch. Int. Pharmacodynam, 92, pp 97–107 (1952)]. For example, cis-4-dimethylamino-3'-phenylspiro[cyclohexane-1,1'(3'H)-isobenzofuran], cis-4-dimethylamino-3'-(4-fluorophenyl)spiro[cyclohexane-1,1'(3'H)-isobenzofuran], cis-3'-(4-chlorophenyl)-4-dimethylaminospiro[cyclohexane-1,1'(3'H)-isobenzofuran]hydrochloride, cis-4-dimethylamino-3'-(4-methylphenyl)spiro[cyclohexane-1,1'(3'H)-isobenzofuran]hydrochloride and trans-4-methylamino-3'-phenylspiro[cyclohexane-1,1'(3'H)-isobenzofuran] at an intraperitoneal dose of 21.9, 14.1, 21.1, 32.1 and 25.0 mg/kg of body weight, respectively, produce a 50% protection from the effect of supramazimal electroshock. These data illustrate that compounds of the present invention are useful in treating convulsions in mammals when administered in amounts ranging from about 0.01 to about 150 mg/kg of body weight per day.

Compounds of the present invention are further useful as analgesics due to their ability to alleviate pain in mammals, as demonstrated in the phenyl-2-quinone writhing assay in mice, a standard assay for analgesia [Proc. Soc. Exptl. Biol. Med., 95, 729 (1957)]. Thus, for example, a subcutaneous dose of 35.9 and 30.4 mg/kg of body weight of 4-amino-3'-phenylspiro[cyclohexane-1,1'(3'H)-isobenzofuran]hydrochloride and 4-amino-3'-cyclohexylspiro[cyclohexane-1,1'(3'H)-isobenzofuran]-hydrochloride, respectively, demonstrate a 50% inhibition of writhing produced in this assay. At a subcutaneous dose of 25 mg/kg of body weight, cis-4-methylamino-3'-phenylspiro[cyclohexane-1,1'(3'H)-isobenzofuran]hydrochloride, cis-4-dimethylamino-3'(4-fluorophenyl)spiro[cyclohexane-1,1'(3'H)-isobenzofuran] and trans-4-methylamino-3'-phenylspiro[cyclohexane-1,1'(3'H)-isobenzofuran]hydrochloride demonstrate a 57%, 69% and 50%, respectively, inhibition of writhing produced in the assay. Also at a subcutaneous dose of 20 mg/kg of body weight cis-3'(4-chlorophenyl)-4-dimethylaminospiro[cyclohexane-1,1'(3'H)-isobenzofuran] demonstrates a 79% inhibition of writhing. These data illustrate that compounds of this invention are useful for alleviating pain in mammals when administered in amounts ranging from about 0.01 to about 100 mg/kg of body weight per day.

Additionally, the compounds of the present invention are useful as tranquilizers as demonstrated by their ability to antagonize the toxicity of amphetamine in aggregated situations in mice [J. Pharmacol. Exp. Therap. 87, 2146 (1946)]. Thus at an intraperitoneal dose of 20 mg/kg of body weight, trans-4-{N-[3-(4-fluorobenzoyl)propyloyl]-N-methyl}amino-3'-phenylspiro[cyclohexane-1,1'(3'H)-isobenzofuran]oxalate and cis-4-{N-[3-(4-fluorobenzoyl)prop-1-yl]-N-methyl}amino-3'(2-methylphenyl)spiro[cyclohexane-1,1'(3'H)-isobenzofuran]hydrochloride antagonize amphetamines toxicity in 90 and 80% of the mice, respectively. These data illustrate that the compounds of the invention are useful as tranquilizers in mammals when administered in amounts ranging from about 0.01 to about 100 mg/kg of body weight.

Other compounds of the invention include:
4-diethylaminospiro[cyclohexane-1,1'(3'H)-isobenzofuran];
4-diisopropylamino-3'-(3-ethylphenyl)spiro[cyclohexane-1,1'(3'H)-isobenzofuran];
4-amino-3'-cyclopropylspiro[cyclohexane-1,1'(3'H)-isobenzofuran];
3'-cyclopropyl-4-dimethylaminospiro[cyclohexane-1,1'-(3'H)-isobenzofuran];
4-diisopropylamino-3'(2-ethylphenyl)spiro[cyclohexane-1,1'(3'H)-isobenzofuran]; and
4-diethylamino-3'-(4-isopropylphenyl)spiro[cyclohexane-1,1'(3'H)-isobenzofuran].

Effective quantities of the compounds of the invention may be administered to a patient by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent, and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following Examples are for illustrative purposes only and are not to be construed as limiting the invention.

EXAMPLE 1 cis-4-Dimethylamino-3'-phenylspiro[cyclohexane-1,1'(3'H)-isobenzofuran]

A solution of 3.4 g of cis-4-dimethylamino-1-{2-[α-methoxy-(phenylmethyl)]phenyl}cyclohexanol, 19 ml of acetic acid and 3.7 ml of hydrochloric acid is heated under reflux for 10 minutes, cooled to 0° C., diluted with 150 ml of water and made basic with 50% sodium hydroxide solution. The precipitate is collected by suction filtration, washed with water and dried to give colorless crystals. Recrystallization from 40 ml of n-hexane gives 78.4% of product, mp 131.5°–132.5° C.

Analysis: Calculated for $C_{21}H_{25}NO$: 82.04%C; 8.20%H; 4.56%N. Found: 82.30%C; 8.21%H; 4.58%N.

EXAMPLE 2 cis-4-Dimethylaminospiro[cyclohexane-1,1'(3'H)-isobenzofuran]-3'-one hydrochloride A solution of 4.50 g of cis-4-dimethylamino-1-[2-(4,5-dihydro-4,4-dimethyl-2-oxazolyl)phenyl]cyclohexanol in 85 ml of 3 N hydrochloric acid is refluxed for 5 hours and then evaporated in vacuo to an oil. The oil is dissolved in 50 ml of dichloromethane, washed with 30 ml of 5% sodium hydroxide solution and with water, dried over anhydrous sodium sulfate and concentrated. The oily residue is dissolved in 20 ml of ethanol. The solution is made acidic with hydrogen chloride/ether and treated with 50 ml of ether. The precipitate is collected by suction filtration and recrystallized from ethanol/ether (50 ml/50 ml) to yield 77.6% of product as colorless crystals, mp 275°–276° C.

Analysis: Calculated for $C_{15}H_{19}NO_2.HCl$: 63.94%C; 7.15%H; 12.58%Cl; 4.97%N. Found: 64.07%C; 7.13%H; 12.31%Cl; 4.86%N.

EXAMPLE 3 cis-4-Dimethylamino-3'-hydroxy-3'-phenylspiro[cyclohexane-1,1'(3'H)-isobenzofuran]

A solution of 8.45 g of cis-4-dimethylaminospiro[cyclohexane-1,1'(3'H)-isobenzofuran]-3-one hydrochloride in 150 ml of dichloromethane is stirred with a solution of 1.28 g of sodium hydroxide in 50 ml of water for ½ hour. The organic phase is separated, washed with water, dried over anhydrous sodium sulfate and concentrated to an oil. The oil is dissolved in 100 ml of dry tetrahydrofuran and added dropwise to 30 ml of cold (−30° C.) stirred 2.1 M phenyllithium in 70:30 benzene-ether. The solution is stirred at 0° C. for 1 hour, diluted wither water and extracted with ether. The organic phase is washed with water, dried over anhydrous sodium sulfate and evaporated to an oil. The oil is diluted with 100 ml of cyclohexane and suction filtered. The filtrate is cooled overnight and the precipitate is collected by suction filtration. The precipitate is recrystallized from 40 ml of methanol. The filter cake and recrystallized material are combined and recrystallized from toluene/hexane (40 ml/50 ml) to provide 32.2% of product, mp 184°–185.5° C.

Analysis: Calculated for $C_{21}H_{25}NO_2$: 77.98%C; 7.79%H; 4.33%N. Found: 78.05%C; 7.85%H; 4.22%N.

EXAMPLE 4 cis-4-Dimethylaminospiro[cyclohexane-1,1'(3'H)-isobenzofuran]hydrochloride

A solution of 5.63 g of 4-dimethylaminospiro[cyclohexane-1,1'(3'H)-isobenzofuran]-3-one hydrochloride in 100 ml of dichloromethane is stirred with a solution of 0.88 g of sodium hydroxide in 40 ml of water. The organic phase is separated, washed with water, dried over anhydrous sodium sulfate and concentrated. The oil is dissolved in 50 ml of dry tetrahydrofuran with stirring. After the addition is complete, the mixture is kept at room temperature for 30 minutes and then refluxed overnight. The solution is cooled to 0° C. and 19 ml of 6 N hydrochloric acid is added dropwise. The mixture is then refluxed for 5 hours and the solvents are evaporated in vacuo to give an oil which is distributed between ether and water. The pH of the aqueous layer is adjusted to 10 with 50% sodium hydroxide solution. The layers are separated and the aqueous layer is extracted with ether. The combined extracts are washed with water, dried over anhydrous sodium sulfate and evaporated to an oil. The oil is dissolved in 40 ml of ethanol and made acidic with a slight excess of hydrogen chloride/ether. After the addition of 60 ml of ether, the precipitate is collected. The precipitate is recrystallized from ethanol/ether (25 ml/35 ml) to give 64.9% of product, mp 248°–249° C.

Analysis: Calculated for $C_{15}H_{21}NO.HCl$: 67.28%C; 8.28%H; 13.24%Cl; 5.23%N. Found: 67.45%C; 8.38%H; 13.15%Cl; 5.03%N.

EXAMPLE 5 cis-Dimethylamino-3'-hydroxy-3'-methylspiro[cyclohexane-1,1'(3'H)-isobenzofuran]

A solution of 5.63 g of cis-4-dimethylaminospiro[cyclohexane-1,1'(3'H)-isobenzofuran]-3one hydrochloride in 150 ml of dichloromethane is stirred for 30 minutes with a solution of 0.90 g of sodium hydroxide in 40 ml of water. The organic phase is washed with water, dried over anhydrous sodium sulfate and concentrated to an oil. The oil is dissolved in 50 ml of dry ether and added dropwise to 11 ml of 2.74 M methylmagnesium chloride in tetrahydrofuran and 10 ml of tetrahydrofuran. The mixture is refluxed for 4 hours, cooled and diluted with 30 ml of water. The organic phase is decanted and the residue is extracted with ether (3×50 ml). The combined organic phase is washed with water (2×50 ml), dried over anhydrous sodium sulfate and concentrated to an oil. The oil is dissolved in 10 ml of ether and 40 ml of hexane is added. After cooling (10 minutes at 5°–10° C.), the precipitate is collected. Recrystallization from toluene/hexane (20 ml/30 ml) provides 59.7% of product, mp 140.5°–141.5° C.

Analysis: Calculated for $C_{16}H_{23}NO$: 73.53%C; 8.87%H; 5.36%N. Found: 73.87%C; 9.10%H; 5.17%N.

EXAMPLE 6 cis-4-Dimethylamino-3'-hydroxy-3'-(4-methylphenyl)-spiro[cyclohexane-1,1'(3'H)-isobenzofuran]

A solution of 5.63 g of cis-4-Dimethylaminospiro[cyclohexane-1,1'(3'H)-isobenzofuran]-3-one hydrochloride in 150 ml of dichloromethane is stirred for 30 minutes with a solution of 0.90 g of sodium hydroxide in 40 ml of water, dried over anhydrous sodium sulfate and concentrated to an oil. The oil is dissolved in 50 ml of dry tetrahydrofuran and added dropwise to 15 ml of 1.96 M 4-methylphenylmagnesium bromide in ether. The mixture is refluxed for 4 hours, cooled and diluted with 30 ml of water. The organic phase is decanted and the residue is extracted with ether (3×50 ml). The combined organic phase is washed with water (2×50 ml), dried over anhydrous sodium sulfate and concentrated to an oil. The oil is crystallized from toluene/hexane (125 ml/75 ml) to provide 60.7% of product, mp 196°197° C.

Analysis: Calculated for $C_{22}H_{27}NO_2$: 78.30%C; 8.06%H; 4.15%N. Found: 78.57%C; 8.08%H; 3.93%N.

EXAMPLE 7 cis-4-Dimethylamino-3'-ethyl-3'-phenylspiro[cyclohexane-1,1'(3'H)-isobenzofuran]hydrochloride To a cold (−50° C.) solution of 4.61 g of cis-4-dimethylamino-3'-phenylspiro[cyclohexane-1,1'(3'H)-isobenzofuran] in 60 ml of dry tetrahydrofuran is added dropwise 15 ml of 2.2 M n-butyllithium in n-hexane. After 30 minutes at −50° C., a solution of 1.60 g (0.0147 M) ethyl bromide in 10 ml of dry tetrahydrofuran is added dropwise. After 1.5 hours at −50° C. and 3 hours at room temperature, 100 ml of water and 200 ml of ether are added. The organic layer is separated, washed with water (2×50 ml), dried over anhydrous sodium sulfate and concentrated to an oil. The oil is dissolved in 30 ml of ethanol and made acidic with a slight excess of hydrogen chloride/ether. After addition of 70 ml of ether and cooling overnight (5° C.), the product is collected by filtration, washed with ether and dried to provide 83.3% of product, mp 266°-267° C.

Analysis: Calculated for $C_{23}H_{29}NO \cdot HCl$: 74.27%C; 8.13%H; 9.53%Cl; 3.77%N. Found: 74.31%C; 8.20%H; 9.39%Cl; 3.57%N.

EXAMPLE 8 cis-4-Dimethylamino-3'-phenyl-3'-(n-propyl)spiro[cyclohexane-1,1'(3'H)-isobenzofuran]hydrochloride To a cold (−50° C.) solution of 3.07 g of cis-dimethylamino-3'-phenylspiro[cyclohexane-1,1'(3'H)-isobenzofuran] in 40 ml of dry tetrahydrofuran is added dropwise 11 ml of 2.1 M n-butyllithium (hexane). After 30 minutes at −50° C., a solution of 1.70 g of n-propyl iodide in 7 ml of dry tetrahydrofuran is added dropwise at −50° C. After 40 minutes at −50° C. and 2 hours at room temperature, 100 ml of water and 200 ml of ether are added. The organic phase is separated, washed with water (3×50 ml), dried over anhydrous sodium sulfate, filtered and concentrated to an oil. The oil is dissolved in 20 ml of ether and made acidic with a slight excess of hydrogen chloride/ether. To this mixture is added 50 ml of ether and the precipitate is isolated by filtration. Recrystallization from ethanol-ether (15 ml-25 ml) provides 57.0% of product, mp 218°-219.5° C.

Analysis: Calculated for $C_{24}H_{31}NO \cdot HCl$: 74.68%C; 8.36%H; 3.63%N; 9.18%Cl. Found: 74.42%C; 8.41%H; 3.26%N; 9.08%Cl.

EXAMPLE 9 cis-4-Dimethylamino-3'-(4-methylphenyl)spiro[cyclohexane-1,1'(3'H)-isobenzofuran]hydrochloride A solution of 2.95 g of 2-[4-(dimethylamino)-1-hydroxyclohexyl]-α-(4-methylphenyl)benzenemethanol in 17 ml of acetic acid and 3 ml of concentrated hydrochloric acid is heated to reflux for 10 minutes. After the solvents are removed under reduced pressure, the residue is dissolved in 100 ml of dichloromethane and concentrated to an oil. The oil is dissolved in 25 ml of ether and the solution is filtered and made acidic with a slight excess of hydrogen chloride/ether. The precipitate is collected by filtration and recrystallized from methanol-ether (5 ml-20 ml) to provide 80.4% of product, mp 243°-244° C.

Analysis: Calculated for $C_{22}H_{27}NO \cdot HCl$: 73.82%C; 7.88%H; 3.91%N; 9.90%Cl. Found: 73.53%C; 7.59%H; 3.68%N; 9.79%Cl.

EXAMPLE 10 cis-4-Dimethylamino-3'-methyl-3'-phenylspiro[cyclohexane-1,1'(3'H)-isobenzofuran]oxalate To a cold (−50° C.) solution of 4.61 g of cis-4-dimethylamino-3'-phenylspiro[cyclohexane-1,1'(3'H)-isobenzofuran] in 50 ml of dry tetrahydrofuran is added dropwise 17 ml of 2.1 M n-butyllithium (hexane). After 30 minutes at −50° C., a solution of 1.87 g of dimethyl sulfate in 8 ml of dry tetrahydrofuran is added dropwise at −50° C. After 45 minutes at −50° C. and 2.5 hours at room temperature, 100 ml of water and 200 of ether are added. The organic phase is separated, washed with water (3×50 ml), dried over anhydrous sodium sulfate, filtered and treated with a solution of 1.8 oxalic acid in 12 ml of ethanol. After cooling (1 hour at 10° C.), the precipitate is collected by filtration, washed with ether and dried. Recrystallization from ethanol/ether (celite) and methanol/ether provides 68.0% of product, mp 176°-178° C.

Analysis: Calculated for $C_{22}H_{27}NO \cdot C_2H_2O_4$: 70.05%C; 7.10%H; 3.40%N. Found: 69.38%C; 7.14%H; 3.21%N.

EXAMPLE 11 cis-4-Dimethylamino-3'-methylspiro[cyclohexane-1,1'(3'H)-isobenzofuran]hydrochloride A solution of 1.94 g of 2-[cis-(4-dimethylamino-1-hydroxycyclohexyl)]-α-methylbenzenemethanol in 30 ml of acetic acid and 4 ml of concentrated hydrochloric acid is heated to reflux for 15 minutes. The solvents are removed under reduced pressure and the oily residue dissolved in 100 ml of dichloromethane. The solution is washed with 5% sodium hydroxide solution, dried over anhydrous sodium sulfate and concentrated to an oil. The oil is dissolved in 20 ml of ether. The solution is made acidic with a slight excess of hydrogen chloride/ether (8/40 ml) to provide 94.7% of product, mp 210°-212° C.

Analysis: Calculated for $C_{16}H_{23}NO \cdot HCl$: 68.19%C; 8.58%H; 12.58%Cl; 4.97%N. Found: 68.38%C; 8.50%H; 12.62%Cl; 5.01%N.

EXAMPLE 12 cis-4-{N-[3-(4-Fluorobenzoyl)-prop-1-yl]-N-methyl}-amino-3'-phenylspiro[cyclohexane-1,1'(3'H)-isobenzofuran]hydrobromide A solution of 2.47 g of cis-4-methylamino-3'-phenylspiro[-cyclohexane-1,1'(3'H)-isobenzofuran]hydrochloride in 25 ml of methanol and 10 ml of water is made basic with 10% sodium hydroxide solution. The solution is diluted with 50 ml of water and after cooling the product is filtered, washed with water and dried to give the starting material (free base), mp 115°–116° C.

A solution of 1.95 g of free base in 35 ml of dimethylformamide is stirred with 1.11 g of potassium iodide, 1.85 g of potassium carbonate and 1.72 g of 4-chloro-p-fluoro-butyrophenone ethylene ketal at 90° C. for 24 hours. The solvent is removed under reduced pressure (0.1 mm) and the residue dissolved in 100 ml of ethanol. The solution is filtered, washed with water, dried over anhydrous sodium sulfate and concentrated to an oil. The oil is dissolved in 10 ml of ethanol and stirred with a slight excess of hydrogen bromide/ether for 1 hour at room temperature. The mixture is diluted with 50 ml of ethanol and the precipitation is collected by suction filtration. Recrystallization from methanol-ether (40/40 ml) provides 61.5% of product, mp 241°–243° C.

Analysis: Calculated for $C_{30}H_{32}FNO_2 \cdot HBr$: 66.91%C; 6.18%H; 3.53%F; 2.60%N. Found: 66.74%C; 6.25%H; 3.48%F; 2.72%N.

EXAMPLE 13

4-Amino-3'-phenylspiro[cyclohexane-1,1'(3'H)-isobenzofuran]hydrochloride

A solution of 6.07 g of 4-oximino-3'-phenylspiro[cyclohexane-1,1'(3'H)-isobenzofuran] in 80 ml of dry tetrahydrofuran is added to a suspension of 2.00 g of lithium aluminum hydride in 60 ml of dry tetrahydrofuran and the mixture is refluxed for 80 minutes. After cooling and hydrolyzing with 25 ml of water the mixture is extracted with 100 ml of ethanol and 50 ml of dichloromethane. The combined organic phase is washed with water, dried over anhydrous potassium carbonate and evaporated to an oil. The oil is dissolved in 100 ml of methanol and the solution is filtered. The filtrate is concentrated in vacuo to a volume of 30 ml and made acidic using hydrogen chloride/ether and 70 ml of ethanol. The precipitate is collected, washed with water and dried. Recrystallization from methanol/ether (40 ml/60 ml) gives 51.6% of product, mp >260° C.

Analysis: Calculated for $C_{19}H_{21}NO \cdot HCl \cdot \frac{1}{4}H_2O$: 71.24%C; 7.08%H; 11.07%Cl; 4.37%N. Found: 71.45%C; 6.92%H; 11.02%Cl; 4.45%N.

EXAMPLE 14

4-Amino-3'-cyclohexylspiro[cyclohexane-1,1'-(3'H)-isobenzofuran]hydrochloride

A mixture of 1.50 g of 4-methoximino-3'-phenylspiro[cyclohexane-1,1'(3'H)-isobenzofuran]hydrochloride, 150 ml of acetic acid and 0.5 g of platinum oxide is hydrogenated at 50 psi and room temperature for 4½ hours. After filtration and removing the solvent, the oily product is dissolved in 100 ml of dichloromethane and washed with 5% sodium hydroxide solution and water. After drying over anhydrous sodium sulfate, the solvent is removed in vacuo to give an oil. The oil is dissolved in 10 ml of methanol and the solution is made acidic using hydrogen chloride/ether. After addition of 50 ml of ether, the precipitate is suction filtered, washed with ether and dried to give 66.0% of product, mp ~220°–224° C.

Analysis: Calculated for $C_{19}H_{27}NO \cdot HCl \cdot \frac{1}{4}H_2O$: 69.92%C; 8.80%H; 10.86%Cl; 4.29%N. Found: 69.80%C; 8.56%H; 11.01%Cl; 4.37%N.

EXAMPLE 15 cis-4-Dimethylamino-3'-hydroxy-3'-(2-methylphenyl)-spiro[cyclohexane-1,1'(3'H)-isobenzofuran]

A 100 ml 3-neck flask equipped with a mechanical stirrer, dropping funnel bearing a nitrogen inlet tube and reflux condenser is charged with 0.804 g of magnesium turnings and 5 ml of anhydrous tetrahydrofuran. The dropping funnel is charged with a solution of 5.13 g of 2-bromotoluene and sufficient anhydrous tetrahydrofuran to give a total volume of 15 ml. A portion (6 ml) of the 2-bromotoluene solution and crystal of iodine are added to the magnesium. The stirred mixture is heated to reflux under nitrogen and refluxed until the reaction initiates. At this point, heating is discontinued and the remaining solution of 2-bromotoluene is added at such a rate as to maintain refluxing. The mixture is refluxed until most of the magnesium dissolves. The dark colored solution is cooled (water bath) and a solution of 6.0 g of cis-4-dimethylaminospiro[cyclohexane-1,1'(3'H)-isobenzofuran]-3'-one and 10 ml of anhydrous tetrahydrofuran is added dropwise over 20 minutes. The resultant suspension is stirred for 20 minutes at room temperature, diluted with 20 ml of tetrahydrofuran and refluxed for 45 minutes. The cooled mixture is quenched by addition of a solution of 8.0 g of ammonium chloride in 35 ml of water. The mixture is suction filtered and the filter cake is washed twice with dichloromethane. The combined filtrates are treated with excess 5% sodium hydroxide solution and 70 ml of dichloromethane. The phases are separated and the aqueous phase is extracted with a total of 500 ml of dichloromethane. The previously extracted filter cake appeared to contain organic material and is washed with methanol. The methanol washings are added to the organic phase. The combined organic phase is dried over anhydrous sodium sulfate, filtered and evaporated to a crisp foam. The foam is crystallized from 40 ml of isopropanol. A small amount of crystalline material separates on cooling to room temperature and the mother liquor is decanted. Cooling and scratching the mother liquor resulted in further crystallization. The mixture is stirred for 24 hours at room temperature and the precipitate is collected by suction filtration and dried in vacuo at 40° C. to afford 49.8% of product, mp 161°–163° C.

Analysis: Calculated for $C_{22}H_{27}NO_2$: 78.30%C; 8.07%H; 4.15%N. Found: 78.12%C; 8.22%H; 3.97%N.

EXAMPLE 16 cis-4-Dimethylamino-3'-(2-methylphenyl)spiro[cyclohexane-1,1'(3'H)-isobenzofuran]

A solution of 3.7 g of cis-4-dimethylamino-3'-hydroxy-3'-(2-methylphenyl)spiro[cyclohexane-1,1'(3'H)-isobenzofuran] and 40 ml of 97% formic acid solution is refluxed with stirring for 2 hours. Excess formic acid is removed on a rotary evaporator at 60° C. and the residue is diluted with 50 ml of water. The solution is made strongly alkaline with 50% sodium hydroxide solution and is extracted thrice with 50 ml portions of dichloromethane. The combined organic phase is dried over anhydrous sodium sulfate, filtered and evaporated to give a solid residue. The residue is dissolved in 35 ml of boiling hexane and the solution is filtered. The filtrate is concentrated to approximately half volume by boiling off the excess hexane. After cooling to room temperature the crystalline precipitate is collected by suction filtration and the filter cake is washed with a little hexane and dried in vacuo at room temperature to afford 74.0% of product, mp 118.5°–119.5° C.

Analysis: Calculated for $C_{22}H_{27}NO$: 82.20%C; 8.47%H; 4.36%N. Found: 82.11%C; 8.64%H; 4.08%N.

EXAMPLE 17 trans-4-Dimethylaminospiro[cyclohexane-1,1'(3'H)-isobenzofuran]-3'-one hydrochloride A 12-1, three-neck flask is charged with 296 of benzanilide and purged overnight with dry nitrogen. Anhydrous tetrahydrofuran (4000 ml) is added and the stirred solution is chilled to −45° C. (benzanilide begins to separate from solution). The stirred suspension is treated with a total of 3.0 M of n-butyllithium in hexane (2.2 M solution). The rate of addition is controlled such that the temperature remains between −30° and −20° C. After addition is complete, the solution is stirred for 60 minutes at 0° C. (ice water bath). During this time the solution becomes red in color. The solution is chilled to −35° to −40° C. and a solution of 105.9 g of 4-dimethylaminocyclohexanone in a little anhydrous tetrahydrofuran is added dropwise over 30 minutes. The resultant red colored turbid mixture is stirred 45 minutes at −40° to −45° C. and then allowed to warm to −10° C. The mixture is stirred at 0° C. (ice water bath) for 1 hour, followed by quenching with 300 ml of water. Dichloromethane (1000 ml) and dilute hydrochloric acid (1500 ml prepared by diluting 420 ml of concentrated hydrochloric acid with water) are added with cooling (internal temperature reaches 32° C.), followed by stirring overnight at room temperature. The phases are separated and the upper dichloromethane phase is washed with a total of 3000 ml of water. The aqueous phases are combined and made strongly alkaline with 50% sodium hydroxide solution. The mixture is extracted with a total of 2500 ml of dichloromethane and the combined extracts are dried over anhydrous sodium sulfate, suction filtered and evaporated to an oil. The volatile amines (aniline, 4-dimethylaminocyclohexanone) are removed by vacuum distillation at 100° C. The residual oil is dissolved in 200 ml of dichloromethane and the solution is diluted with anhydrous ether (2000 ml). A small amount of amorphorous precipitate is removed by filtration. The filtrate is treated with excess ethereal hydrochloric acid and the resultant suspension is stirred for 45 minutes to break up the aggregates. The crystalline precipitate is collected by suction filtration and the filter cake is washed twice with ether, and dried in vacuo at 35° C. overnight over sodium hydroxide pellets. Recrystallization from 550 ml of methanol (the solution is allowed to stand overnight at room temperature) affords 14.0% of the trans-isomer, mp 275°–283° C.

Analysis: Calculated for $C_{15}H_{19}NO_2 \cdot HCl$: 63.93%C; 7.15%H. Found: 63.87%C; 7.16%H.

Evaporation of the filtrate and recrystallization of the residue from isopropanol provides 38.7% of the cis-isomer.

EXAMPLE 18 trans-4-Dimethylamino-3'-hydroxy-3'-phenylspiro[cyclohexane-1,1'(3'H)-isobenzofuran]

A 250 ml three-neck flask equipped with a mechanical stirrer, reflux condenser and 50 ml dropping funnel bearing a nitrogen inlet tube is charged with 2.19 g of magnesium turnings and 14 ml of anhydrous tetrahydrofuran. The system is flushed with dry nitrogen and the dropping funnel is charged with a solution of 14.13 g of bromobenzene and 50 ml of anhydrous tetrahydrofuran. A portion (10 ml) of the bromobenzene solution is added at once and the stirred mixture is heated to reflux (steam bath). After initiation of the reaction, heating is discontinued and the remainder of the bromobenzene solution is added at such a rate as to maintain reflux. After addition is complete, the mixture is heated under reflux until most of the magnesium has dissolved. The phenylmagnesium bromide solution is chilled (10° C.) and a solution of trans-4-dimethylaminospiro[cyclohexane-1,1'(3'H)-isobenzofuran]-3'-one and 100 ml of anhydrous tetrahydrofuran is added dropwise over 45 minutes with stirring and cooling. After the addition is complete, the mixture is stirred 15 minutes at room temperature, followed by refluxing for 40 minutes. To the cooled mixture is added a solution of 24.0 g of ammonium chloride and 80 ml of water with stirring. The mixture is suction filtered and the filter cake is washed twice with dichloromethane. The combined filtrates are treated with excess 5% sodium hydroxide solution and additional dichloromethane is added. The phases are separated and the aqueous phase is extracted twice with dichloromethane. The combined organic phase is dried over anhydrous sodium sulfate, suction filtered and evaporated to an oil which foamed. Trituration with dichloromethane and evaporation affords a solid. The filter cake containing magnesium salts is suspended in 100 ml of 5% sodium hydroxide solution and stirred several minutes. The mixture is suction filtered and the filter cake is washed twice with methanol. The combined filtrates are extracted with dichloromethane to provide an additional amount of solid. Recrystallization of the combined solids from 125 ml of toluene affords product, mp 179°–185° C. Further treatment of the filter cake with alkali (stirred three days at room temperature with 100 ml of 5% sodium hydroxide solution and 50 ml of dichloromethane affords additional product, mp 184°–188° C. Total yield 73.1%.

Analysis: Calculated for $C_{21}H_{25}NO_2$: 77.98%C; 7.79%H; 4.33%N. Found: 78.16%C; 7.39%H; 3.98%N.

EXAMPLE 19 trans-4-Dimethylamino-3'-phenylspiro[cyclohexane-1,1'(3'H)-isobenzofuran]

A solution of 3.7 g of trans-4-dimethylamino-3'-hydroxy-3'-phenylspiro[cyclohexane-1,1'(3'H)-isobenzofuran] and 42 ml of 97% formic acid solution is heated under reflux for 2.0 hours. Excess formic acid is removed under reduced pressure and the residue is dissolved in 200 ml of water. The solution is made alkaline with 5% sodium hydroxide solution and extracted thrice with 100 ml portions of dichloromethane. The combined organic phase is dried over anhydrous sodium sulfate, suction filtered and evaporated under reduced pressure to a yellow colored solid. Recrystallization from 10 ml of acetonitrile affords 66.2% of product, mp 83.5°–85° C.

Analysis: Calculated for $C_{21}H_{25}NO$: 82.04%C; 8.20%H; 4.56%N. Found: 82.25%C; 8.41%H; 4.54%N.

EXAMPLE 20 trans-4-methylphenoxycarbonylamino-3'-phenylspiro[cyclohexane-1,1'(3'H)-isobenzofuran]

A stirred solution of 4.61 g of trans-4-dimethylamino-3'-phenylspiro[cyclohexane-1,1'(3'H)-isobenzofuran] and 20 ml of sieve dried dichloromethane is treated dropwise over one hour with a solution of 2.82 g of phenylchloroformate and 15 ml of sieve dried dichloromethane. The resultant solution is stirred overnight at room temperature during which a colorless precipitate separates. Evaporation under reduced pressure affords a gel which fails to solidify on trituration with anhydrous ether. The mixture is evaporated and the residue is dissolved in dichloromethane and washed with 15 ml each of water and 5% sodium hydroxide solution. The dried anhydrous sodium sulfate organic phase is concentrated under reduced pressure to a slightly turbid, viscous oil. The oil is dissolved in 30 ml of dichloromethane and the solution is treated with 1.0 g of phenylchloroformate, followed by stirring for 96 hours at room temperature with exclusion of moisture. Work up as described in Example 23, and trituration with ether affords a solid which is collected by suction filtration. The solid is dissolved in 70 ml of dichloromethane and the solution is washed with 5% sodium hydroxide solution. The organic phase is dried over anhydrous sodium sulfate, suction filtered and evaporated to an oil which solidifies on trituration with ether. Recrystallization of the solid from 18 ml of 95% ethanol affords 37.1% of product, mp 127°–134° C.

Analysis: Calculated for $C_{27}H_{27}NO_3$: 78.42%C; 6.58%H; 3.39%N. Found: 78.39%C; 6.58%H; 3.08%N.

EXAMPLE 21 cis-4-Dimethylamino-3'-(4-fluorophenyl)-3'-hydroxyspiro[cyclohexane-1,1'(3'H)-isobenzofuran]hemihydrate A 10 ml portion of a solution of 24 g of 4-bromofluorobenzene and 50 ml of anhydrous tetrahydrofuran is added to a mixture of 3.72 g of magnesium turnings and 20 ml of anhydrous tetrahydrofuran. The mixture is heated (steam bath) with stirring until the reaction initiates and the steam bath is removed. The remaining 4-bromofluorobenzene solution is then added at such a rate as to maintain a gentle reflux. After addition is complete, the mixture is heated under reflux until most of the magnesium dissolves. The dark colored solution is cooled (10° C., bath temperature) and diluted with 50 ml of anhydrous tetrahydrofuran. To the cooled, stirred solution is added dropwise over 15 minutes, a filtered solution of cis-4-dimethylaminospiro[cyclohexane-1,1'(3'H)-isobenzofuran]-3'-one (29.0 g) and 70 ml of anhydrous tetrahydrofuran. The resultant dark colored solution is stirred for 15 minutes at 15° C., and 60 minutes at room temperature, during which time a precipitate separates. The mixture is heated under reflux for 50 minutes, cooled and allowed to stand overnight at room temperature. The mixture is decanted into 250 ml of water, made alkaline with 5% sodium hydroxide solution and suction filtered. The filter cake is extracted with four 100 ml portions of dichloromethane using each extract to wash the aqueous phase. The combined dried anhydrous sodium sulfate organic phase is evaporated to afford a crude product. Recrystallization from 50 ml of 95% ethanol affords an impure product and additional impure product is obtained from the mother liquor. The filter cake of magnesium salts is treated with three 200 ml portions of dichloromethane and a little methanol. The combined, dried anhydrous sodium sulfate organic phase affords a crude material, which after recrystallization from 200 ml of 95% ethanol provides a reasonably pure product, mp 140°–158° C. The mother liquor provides additional material. Recrystallization from 100 ml of 95% ethanol affords additional product, mp 140°–159° C. The total yield of purified material is 54.2%.

Analysis: Calculated for $C_{21}H_{24}FNO_2.0.5H_2O$: 71.98%C; 7.19%H; 4.00%N; 5.42%F. Found: 71.52%C; 7.27%H; 3.87%N; 5.28%F.

A dried (Abderhalden pistol, toluene) sample has Analysis: Calculated for $C_{21}H_{24}FNO_2$: 73.87%C; 7.08%H; 4.10%N. Found: 73.33%C; 7.11%H; 3.86%N.

EXAMPLE 22 cis-4-Dimethylamino-3'-(4-fluorophenyl)spiro[cyclohexane-1',1'(3'H)-isobenzofuran]

A solution of 5.12 g of cis-4-dimethylamino-3'-(4-fluorophenyl)-3'-hydroxypspiro[cyclohexane-1,1'(3'H)-isobenzofuran] and 50 ml of 97% formic acid is heated 2 hours under reflux with stirring. Excess formic acid is removed under reduced pressure and the residue is dissolved in 200 ml of water. The solution is made alkaline with 5% sodium hydroxide solution and extracted thrice with 100 ml portions of dichloromethane. The organic phase is dried over anhydrous sodium sulfate, suction filtered and evaporated to afford a yellow colored solid. Recrystallization from 15 ml of acetonitrile affords a green colored solid. Recrystallization of this solid from 15 ml of acetonitrile with decolorization (Darco G60 activated carbon) provides 30% of product, mp 104.5°–106° C.

Analysis: Calculated for $C_{21}H_{24}FNO$: 77.51%C; 7.43%H; 4.30%N; 5.84%F. Found: 77.60%C; 7.47%H; 4.07%N; 5.92%F.

EXAMPLE 23 cis-4-Methylphenoxycarbonylamino-3'-(2-methylphenyl)spiro[cyclohexane-1,1'(3'H)-isobenzofuran]

A stirred, cooled (bath temperature 15° C.) solution of 6.42 g of cis-4-dimethylamino-3'-(2-methylphenyl)-spiro[cyclohexane-1,1'(3'H)-isobenzofuran] and 20 ml of sieve dried dichloromethane is treated with exclusion of moisture over 40 minutes with a solution of 3.45 g of redistilled phenylchloroformate and 20 ml of dichloromethane. The resultant solution is stirred for 24 hours at room temperature and is then allowed to stand for 24 hours at room temperature with exclusion of moisture. The solution is washed thoroughly with 30 ml each of 5% sodium hydroxide solution and water, dried over anhydrous sodium sulfate and evaporated to an oil which forms a crisp, dry foam. Crystallization from 150 ml of hexane with filtration provides 65.5% of product, mp 122°–125.5° C.

Analysis: Calculated for $C_{28}H_{29}NO_3$: 78.66%C; 6.84%H; 3.28%N. Found:

EXAMPLE 24 trans-4-Methylamino-3'-phenylspiro[cyclohexane-1,1'(3'H)-isobenzofuran]hydrochloride A stirred suspension of 5.82 g of trans-4-methylphenoxycarbonylamino-3'-phenylspiro[cyclohexane-1,1'(3'H)-isobenzofuran] and alcoholic potassium hydroxide [prepared from 8.25 g of potassium hydroxide pellets, 2.5 ml of water and 58 ml of n-propanol] is heated overnight under reflux. Excess n-propanol is removed from the cooled solution on a rotary evaporator and the residual syrup is diluted with water and extracted twice with 125 ml portions of dichloromethane. The combined, dried over anhydrous sodium sulfate organic phase is filtered and concentrated to an oil. A solution of the oil and 50 ml of anhydrous ether is filtered and treated with a slight excess of ethereal hydrogen chloride. The precipitate is collected by suction filtration and dried in vacuo at room temperature over sodium hydroxide pellets. Recrystallization of the crude product from 160 ml of 95% ethanol affords 44.9% of product, mp 286°–290° C. (dec).

Analysis: Calculated for $C_{20}H_{23}NO.HCl$: 72.82%C; 7.33%H; 4.25%N; 10.75%Cl. Found: 72.78%C; 7.67%H; 4.25%N; 10.69%Cl.

EXAMPLE 25 cis-4-Methylamino-3'-(2-methylphenyl)spiro[cyclohexane-1,1'(3'H)-isobenzofuran]

A stirred suspension of 12 g of cis-4-methylphenoxycarbonylamino-3'-(2-methylphenyl)spiro[cyclohexane-1,1'(3'H)-isobenzofuran] and alcoholic potassium hydroxide [prepared from 16.5 g of potassium hydroxide pellets, 5 ml of water and 80 ml of n-propanol] is heated overnight under reflux. Excess n-propanol is removed from the cooled solution on a rotary evaporator. The residue is diluted with water and extracted thrice with 150 ml portions of dichloromethane. The dried anhydrous sodium sulfate organic phase is evaporated to an oil. Work up as described in Example 24 affords 10.3 g of crude oil, which is dissolved in 50 ml of anhydrous ether and treated with excess ethereal hydrochloric acid. The precipitate is collected by suction filtration, washed once with anhydrous ether and dried in vacuo at room temperature over sodium hydroxide pellets. Recrystallization of the crude product from 700 ml of isopropanol affords 53.5% of product, mp 275°–277.5° C.

Analysis: Calculated for $C_{21}H_{25}NO.HCl$: 73.56%C; 7.35%H; 4.09%N; 10.34%Cl. Found: 73.22%C; 7.73%H; 3.83%N; 10.04%Cl.

EXAMPLE 26 cis-3'-(4-Fluorophenyl)-4-methylphenoxycarbonylaminospiro[cyclohexane-1,1'(3'H)-isobenzofuran]

A stirred solution of 3.07 g of cis-4-dimethylamino-3'-(4-fluorophenyl)spiro[cyclohexane-1,1'(3'H)-isobenzofuran] and 7 ml of sieve dried dichloromethane is treated over 2 minutes with a solution of 1.62 g of redistilled phenylchloroformate and 7 ml of dichloromethane with water bath cooling. The resultant solution is stirred overnight at room temperature with exclusion of moisture and is then allowed to stand five days at room temperature. The solution is diluted with 70 ml of dichloromethane and washed thoroughly with 5% sodium hydroxide solution. The organic phase is dried over anhydrous sodium sulfate and evaporated to an amorphorous solid. Recrystallization from 50 ml of 95% ethanol affords 73.3% of product, mp 133°–137° C.

Analysis: Calculated for $C_{27}H_{26}FNO_3$: 75.15%C; 6.07%H; 3.25%N. Found: 74.87%C; 6.23%H; 3.09%N.

EXAMPLE 27 cis-3'-(4-Chlorophenyl)-4-dimethylamino-3'-hydroxyspiro[cyclohexane-1,1'(3'H)-isobenzofuran]

To 0.87 g of magnesium turnings and 7 ml of anhydrous tetrahydrofuran is added 5 ml of a solution of p-bromochlorobenzene (6.89 g) and 15 ml of anhydrous tetrahydrofuran (nitrogen atmosphere). The stirred mixture is heated (steam bath) to reflux to initiate formation of the Grignard reagent. The steam bath is removed and the remaining solution of p-bromochlorobenzene is added at such a rate as to maintain a gently reflux. The resultant solution is heated under reflux until most of the magnesium dissolves, followed by cooling with a water bath. A solution of 7.36 g of cis-4-dimethylaminospiro[cyclohexane-1,1'(3'H)-isobenzofuran]-3'-one and 10 ml of anhydrous tetrahydrofuran is added dropwise over 15 minutes, followed by stirring for 15 minutes. The brown solution is heated under reflux for 30 minutes during which a brown precipitate separates. The mixture is then stirred for 3 hours at room temperature and allowed to stand overnight at room temperature. The mixtured is poured into water (100 ml) and made alkaline with 5% sodium hydroxide solution. The mixture is suction filtered and the filter cake is washed well with dichloromethane and methanol. The filtrates are combined and diluted with methanol to a total volume of 500 ml. The resultant precipitate is removed by suction filtration and the filtrate is concentrated to remove the organic solvents. The residual suspension is extracted thrice with 200 ml portions of dichloromethane and the combined extracts dried over anhydrous sodium sulfate for 2 days. The mixture is suction filtered and the filter cake is extracted with methanol to remove what appeared to be a crystalline precipitate. The filtrates are combined and evaporated to an amorphorous solid. The solid is dissolved in 30 ml of isopropanol and filtered to remove an insoluble material. The filtrate is evaporated to an amorphorous solid. A solution of the solid in diethyl ether is filtered and the filtrate evaporated to an amorphorous solid. Two recrystallizations from acetonitrile and drying in an Abderhalden pistol (95% ethanol) affords 9.3% of product, mp 164°–168° C.

Analysis: Calculated for $C_{21}H_{24}ClNO_2$: 70.48%C; 6.76%H; 3.91%N; 9.91%Cl. Found: 70.30%C; 6.84%H; 4.00%N; 9.70%Cl.

EXAMPLE 28 cis-3'-(4-Chlorophenyl)-4-dimethylaminospiro[cyclohexane-1,1'(3'H)-isobenzofuran]

A stirred solution of 6.92 g of cis-3'-(4-chlorophenyl)-4-dimethylamino-3'-hydroxyspiro[cyclohexane-1,1'(3'H)-isobenzofuran] and 35 ml of 97% formic acid is heated under reflux for 2.5 hours. Excess formic acid is removed on a rotary evaporator, the residual syrup diluted with 150 ml of water and the solution made alkaline with 10% sodium hydroxide solution. The mixture is extracted thrice with 150 ml portions of dichloromethane and the combined extracts are dried over anhydrous sodium sulfate. After filtration and concentration of the filtrate, the residual oil is dissolved in 150 ml of anhydrous ether, the solution filtered and acidified with ethereal hydrogen chloride. The precipitate is collected, washed twice with anhydrous ether and dried at 40° C. to afford crude material. Repeated recrystallization from isopropanol affords 20.9% of product, mp 251°–253° C.

Analysis: Calculated for $C_{21}H_{24}ClNO \cdot HCl \cdot H_2O$: 63.63%C; 6.87%H; 3.53%N. Found: 63.48%C; 6.51%H; 3.36%N.

EXAMPLE 28 A cis-3'-(4-Chlorophenyl)-4-dimethylaminospiro[cyclohexane-1,1'(3'H)-isobenzofuran]

A stirred solution of 8.42 g of cis-3'-(4-chlorophenyl)-4-dimethylamino-3'-hydroxyspiro[cyclohexane-1,1'(3'H)-isobenzofuran] and 40 ml of 97% formic acid solution is heated 2 hours under reflux. Excess formic acid is removed on a rotary evaporator and the residual oil is diluted with 75 ml of water. The solution is made alkaline with excess 10% sodium hydroxide solution, followed by extraction with three 60 ml portions of dichloromethane. The combined organic phase is dried over anhydrous sodium sulfate, vacuum filtered and concentrated to an oil which is subjected to azeotropic distillation with 50 ml of toluene. The precipitate is isolated by vacuum filtration and washed with hexane. Drying in vacuo at 35° C. affords 91.5% of product, mp 110°–113° C.

Analysis: Calculated for $C_{21}H_{24}ClNO$: 73.78%C; 7.08%H. Found: 73.71%C; 7.02%H.

EXAMPLE 29 cis-3'-(4-Fluorophenyl)-4-methylaminospiro[cyclohexane-1,1'(3'H)-isobenzofuran]

A stirred suspension of 4.54 g of cis-3'-(4-fluorophenyl)-4-methylphenoxycarbonylaminospiro[cyclohexane-1,1'(3'H)-isobenzofuran], 6.0 g of potassium hydroxide pellets. 2.5 ml of water and 40 ml of n-propanol is heated under reflux overnight. Dilution with water, removal of n-propanol on a rotary evaporator and extraction with two 100 ml portions of dichloromethane affords a crude oil after evaporation. A solution of the oil and 50 ml of anhydrous ether is treated with excess ethereal hydrogen chloride. The precipitate is collected, washed twice with anhydrous ether and dried in vacuo at 40° C. over sodium hydroxide pellets. Recrystallization of the crude material from 50 ml of isopropanol and drying in an Abderhalden pistol (toluene) affords 54% of product, mp 263°–267° C.

Analysis: Calculated for $C_{20}H_{22}FNO \cdot HCl \cdot 0.5H_2O$: 67.69%C; 6.25%H; 3.95%N. Found: 67.96%C; 6.64%H; 3.99%N.

EXAMPLE 30 trans-4-{N-{3-[2-(4-Fluorophenyl)-1,3-dioxalon-2-yl]propyl}-N-methyl}amino-3'-phenylspiro[cyclohexane-1,1'(3'H)-isobenzofuran]

A stirred mixture of 2.70 g of trans-4-methylamino-3'-phenylspiro[cyclohexane-1,1'(3'H)-isobenzofuran], 1.82 g of powdered potassium iodide, 1.82 g of anhydrous sodium bicarbonate, 2.81 g of 2-(3-chloropropyl)-2-(4-fluorophenyl)-1,3-dioxolan and 55 ml of sieve dried dimethylformamide is heated at 90° C. overnight with exclusion of moisture. The cooled mixture is diluted with 80 ml of dichloromethane, vacuum filtered and the filtrate is concentrated to an oil. A solution of the oil and 100 ml of dichloromethane is washed once with 70 ml of 0.3 N sodium hydroxide solution and twice with 50 ml portions of water. The organic phase is dried over anhydrous sodium sulfate, filtered and evaporated to an oil which crystallizes on standing. Trituration with hexane affords a crystalline material which is vacuum filtered. Recrystallization from 15 ml of 95% ethanol affords 43% of product, mp 92°–94° C.

Analysis: Calculated for $C_{32}H_{36}FNO_3$: 76.61%C; 7.25%H. Found: 76.50%C; 7.21%H.

EXAMPLE 31 cis-3'(4-Chlorophenyl)-4-methylphenoxycarbonylaminospiro[cyclohexane-1,1(3'H)-isobenzofuran]

A mixture of 1.60 g of cis-3'-(4-chlorophenyl)-4-dimethylaminospiro[cyclohexane-1,1'(3'H)-isobenzofuran]-hydrochloride monhydrate, 100 ml of dichloromethane and 50 ml of 10% sodium hydroxide solution is thoroughly agitated, the phases separated and the organic phase dried over anhydrous sodium sulfate. Concentration of the organic phase affords an oil which is dissolved in 10 ml of dichloromethane and treated with 1.16 g of anhydrous anhydrous potassium carbonate and a solution of 1.32 g of redistilled phenylchloroformate and 10 ml of dichloromethane. The stirred suspension is heated under reflux overnight with exclusion of moisture. The cooled mixture is vacuum filtered. The filtrate is diluted with 70 ml of dichloromethane, washed thoroughly with excess 10% sodium hydroxide solution, dried over anhydrous sodium sulfate, vacuum filtered and concentrated to an oil. Two recrystallizations from 95% ethanol affords 53% of product, mp 127°–133° C.

Analysis: Calculated for $C_{27}H_{26}ClNO_3$: 72.39%C; 5.88%H. Found: 72.20%C; 5.86%H.

EXAMPLE 32 trans-4-[(3-p-Fluorobenzyl-prop-1-yl)methylamino]-3'-phenylspiro[cyclohexane-1,1'(3'H)-isobenzofuran]oxalate A stirred solution of 4.46 g of trans-4-{N-{3-[2-(4-fluorophenyl)-1,3-dioxolan-2-yl]propyl}-N-methyl}-amino-3'-phenylspiro[cyclohexane-1,1'(3'H)-isobenzofuran], 70 ml of methanol and 40 ml of 3 N hydrochloric acid is heated 2 hours under reflux, followed by standing at ambient temperature overnight. A crystalline precipitate separates on standing and is collected by vacuum filtration. The filter cake is washed twice with ether and dried at 40° C. over sodium hydroxide pellets in vacuo. A solution of 3.3 g of the crude product and 70 ml of dichloromethane is washed with excess 10% sodium hydroxide solution, dried over anhydrous sodium sulfate and evaporated to an oil. A solution of this oil and 15 ml of methanol is treated with a solution of 0.675 g of oxalic acid and 10 ml of methanol. The resultant solution is concentrated to afford a tacky foam which is triturated with ether. The resultant precipitate is collected by vacuum filtration and dried at ambient temperature in vacuo. Recrystallization of the crude material from 15 ml of 95% ethanol affords 41.7% of product, mp 161°–163° C.

Analysis: Calculated for $C_{30}H_{32}FNO_2 \cdot C_2H_2O_4$: 70.17%C; 6.27%H. Found: 70.24%C; 6.23%H.

EXAMPLE 33 cis-4-{N-[3-(4-Fluorobenzoyl)prop-1-yl]-N-methyl}-amino-3'-(2-methylphenyl)spiro[cyclohexane-1,1'(3'H)-isobenzofuran]hydrochloride A solution of 4.50 g of cis-4-methylamino-3'-(2-methylphenyl)spiro[cyclohexane-1,1'(3'H)-isobenzofuran]hydrochloride and 70 ml of dichloromethane is washed with excess 10% sodium hydroxide solution.

The organic phase is dried over anhydrous sodium sulfate, filtered and evaporated to afford an oil which crystallizes. A stirred suspension of the crystalline free base, 2.61 g of finely powdered potassium iodide, 2.69 g of anhydrous sodium carbonate, 3.67 g of 4-chloro-p-fluorobutyrophenone ethylene ketal and 55 ml of dichloromethane is heated at 90° C. (bath temperature) overnight with exclusion of moisture. The cooled mixture is diluted with 80 ml of dichloromethane and vacuum filtered. The filtrate is concentrated on a rotary evaporator and the residual oil is dissolved in 125 ml of dichloromethane. The solution is washed with 70 ml of 10% sodium hydroxide solution, 70 ml of water and dried over anhydrous sodium sulfate. The mixture is vacuum filtered and the filtrate is concentrated to afford an oil which is dissolved in 150 ml of anhydrous ether. A precipitate separates and the mixture is filtered through a pad of anhydrous sodium sulfate. The filtrate is treated with ethereal hydrogen chloride whereupon a viscous gum separates. The gum is dissolved in 7 ml of absolute ethanol and the solution is gradually diluted with 150 ml of anhydrous ether. Collection of the precipitate by vacuum filtration and drying affords a crude material. Recrystallization from 400 ml of isopropanol affords 20.3% of product, mp 253°–254° C. (dec). Concentration of the mother liquor and trituration of the residue with 50 ml of hot isopropanol affords an additional 12.4% of product, mp 251°–254° C. (dec).

Analysis: Calculated for $C_{31}H_{34}FNO_2 \cdot HCl$: 73.27%C.; 6.96%H. Found: 73.19%C; 7.03%H.

EXAMPLE 34 cis-3'-(4-Chlorophenyl)-4-methylaminosprio[cyclohexane-1,1'(3'H)-isobenzofuran]hydrochloride A stirred suspension of 6.26 g of cis-3'-(4-chlorophenyl)-4-methylphenoxycarbonylaminospiro[cyclohexane-1,1'(3'H)isobenzofuran], 7.85 g of potassium hydroxide pellets, 3.0 ml of water and 35 ml of n-propanol is heated under reflux for 24 hours. The solution is concentrated to a syrup, diluted with 150 ml of water and extracted thrice with 50 ml portions of dichloromethane. The organic phase is dried over anhydrous sodium sulfate, filtered and concentrated to an oil. A solution of the oil and 75 ml of anhydrous ether is treated with ethereal hydrogen chloride. The precipitate is collected by vacuum filtration, washed twice with ether and dried over sodium hydroxide pellets in vacuo at 40° C. Recrystallization of the crude product from 175 ml of absolute ethanol affords a product, mp 275°–277° C. (dec). Refrigeration of the mother liquor affords a second crop of colorless crystalline material, mp 275°–280° C. (dec). Total yield 45.8%.

Analysis: Calculated for $C_{20}H_{22}ClNO \cdot HCl$: 65.94%C; 6.36%H; 3.85%N. Found: 66.13%C; 6.44H; 3.77%N.

EXAMPLE 35 cis-3'-(4-Chlorophenyl)-4-{N-[3-(4-fluorobenzoyl)prop-1-yl]-N-methyl}aminospiro[cyclohexane-1,1'(3'H)-isobenzofuran]hydrochloride A suspension of 4.07 g of cis-3'-(4-chlorophenyl)-4-methylaminospiro[cyclohexane-1,1'(3'H)-isobenzofuran]hydrochloride and 70 ml of methanol is treated with 10 ml of 10% sodium hydroxide solution. The methanol is removed on a rotary evaporator and the residue is diluted with 100 ml of water and extracted thrice with 70 ml portions of dichloromethane. The combined organic phase is dried over anhydrous sodium sulfate, filtered and concentrated to an oil. A stirred suspension of the oil, 2.06 g of potassium iodide, 2.08 g of anhydrous sodium bicarbonate, 3.06 g of 4-chloro-p-fluorobutyrophenone ethylene ketal and 50 ml of sieve dried dimethylformamide is held at 88°–90° C. (bath temperature) overnight with exclusion of moisture. The cooled mixture is diluted with 100 ml of dichloromethane, vacuum filtered and the filtrate concentrated at 40°–90° C. on a rotary evaporator. The solid residue is diluted with 100 ml of water and extracted with a total of 200 ml of dichloromethane. The organic phase is washed with 50 ml of 10% sodium hydroxide solution, 50 ml of water, dried over anhydrous sodium sulfate, vacuum filtered and concentrated to an oil. A solution of the oil and 100 ml of anhydrous ether is treated with excess ethereal hydrogen chloride. A gum separates. A solution of the gum, 70 ml of methanol and 40 ml of 3 N hydrochloric acid solution is heated under reflux for 1.5 hours, then allowed to stand overnight at ambient temperature. The solution is decanted from a small amount of tar and the methanol is evaporated. The residue is made alkaline with 10% sodium hydroxide solution and extracted with a total of 200 ml of dichloromethane. The dried (anhydrous sodium sulfate) organic phase is concentrated to an oil which is dissolved in 300 ml of anhydrous ether and filtered to remove an amorphorous precipitate. The filtrate is treated with ethereal hydrogen chloride and the precipitate is collected by vacuum filtration and dried to afford a crude material. Recrystallization from 150 ml of acetonitrile affords 18.6% of product, mp 240°–242° C. (dec).

Analysis: Calculated for $C_{30}H_{31}ClFNO_2 \cdot HCl$: 68.17%C; 6.12%H; 2.65%N. Found: 67.90%C; 5.97%H; 2.40%N.

EXAMPLE 36 cis-4-{N-[3-(4-Fluorobenzoyl)prop-1-yl]-N-methyl}-amino-3'-(4-fluorophenyl)spiro[cyclohexane-1,1'(3'H)-isobenzofuran]hydrochloride A stirred suspension of 4.26 g of cis-3'-(4-fluorophenyl)-4-methylaminospiro[cyclohexane-1,1'(3'H)-isobenzofuran], 2.61 g of potassium iodide, 2.69 g of anhydrous sodium bicarbonate, 3.67 g of 2-(3-chloropropyl)-2-(4-fluorophenyl)-1,3-dioxolane and 50 ml of sieve dried dimethylformamide is held at 90° C. overnight with exclusion of moisture. The cooled mixture is diluted with 60 ml of dichloromethane, vacuum filtered and concentrated on a rotary evaporator to an oil. A solution of the oil and 100 ml of dichloromethane is washed with 100 ml of 10% sodium hydroxide solution, dried over anhydrous sodium sulfate, filtered and the filtrate concentrated to an oil. A filtered solution of the oil and 100 ml of anhydrous ether is treated with ethereal hydrogen chloride. The precipitated gum is triturated with fresh ether to afford a yellow powder which is dried at 40° C. over sodium hydroxide pellets. A stirred solution of the crude ketal hydrochloride, 70 ml of methanol and 40 ml of 3 N hydrochloric acid is heated under reflux for 1.5 hours and allowed to stand overnight at ambient temperature. The mixture is vacuum filtered and the filtrate concentrated on a rotary evaporator to remove the methanol. The residue is made alkaline with 10% sodium hydroxide solution and extracted with dichloromethane. The organic phase is washed with water, dried over anhydrous sodium sulfate, filtered and evaporated to an oil. A solution of the oil and 70 ml of anhydrous ether is filtered through anhydrous sodium sulfate and the filtrate is treated with ethereal hydrogen chloride. Recrystallization of the precipitate from 50 ml of 95% ethanol affords 30% of product, mp 230°–233° C.

Analysis: Calculated for $C_{30}H_{31}F_2NO_2.HCl$: 70.36%C; 6.31%H; 2.74%N. Found: 70.29%C; 6.35%H; 2.68%N.

EXAMPLE 37

4-Methylamino-3'-phenylspiro[cyclohexane-1,1'(3'H)-isobenzofuran]hydrochloride

A solution of 7.90 g of 4-(ethoxycarbonylmethylamino)-3'-phenylspiro[cyclohexane-1,1'(3'H)-isobenzofuran] in 50 ml of ethanol and 60 ml of ethylene glycol is refluxed with 10 ml of 50% sodium hydroxide for 20 hours. Ethanol is distilled and the mixture is heated for 1 hour at 150° C. After cooling, the mixture is diluted with 100 ml of water and extracted with ether (3×100 ml). The ethereal solution is washed with water, dried over anhydrous sodium sulfate, filtered, diluted with 50 ml of ethanol and made acidic with a slight excess of hydrogen chloride/ether. The precipitate is collected by suction filtration and recrystallized from hydrogen chloride/ether (110 ml/100 ml) to provide 49.3% of product, mp 268°–272° C.

Analysis: Calculated for $C_{20}H_{23}NO.HCl$: 72.82%C; 7.33%H; 10.75%Cl; 4.25 N. Found: 72.58%C; 7.16%H; 10.64%Cl; 4.16%N.

EXAMPLE 38 cis-4-Dimethylamino-1-{2-[α-methoxy-(phenylmethyl)]phenyl}cyclohexanol

To a cold (−50° C.) stirred solution of 27.7 g of 2-bromobenzhydryl methyl ether in 50 ml of dry tetrahydrofuran is added dropwise under nitrogen 60 ml of 2.4 M n-butyllithium in hexane. The solution is stirred at −60° C. for 2 hours and a solution of 13.8 g of 4-dimethylaminocyclohexanone in 25 ml of dry tetrahydrofuran is added over 15 minutes at −40° to −50° C. The mixture is stirred at −70° to 0° C. overnight. After addition of 50 ml of water and 50 ml of n-hexane, the mixture is transferred to a separatory funnel and the organic phase washed with water (3×50 ml), dried over anhydrous sodium sulfate and evaporated to an oil. To the oil is added 300 ml of n-hexane and after cooling, crystals are collected by suction filtration. Recrystallization from acetone/hexane (25 ml/100 ml) provides 32.4% of product as colorless crystals, mp 120°–121° C.

Anlaysis: Calculated for $C_{22}H_{29}NO_2$: 77.84%C; 8.61%H; 4.13% N. Found: 78.12%C; 8.64%H; 3.92%N.

EXAMPLE 39 cis-4-Dimethylamino-1-[2-(4,6-dihydro-4,4-dimethyl-2-oxazolyl)phenyl]cyclohexanol A cold (−35° C.) stirrled solution of 25.4 g of 2-(2-bromophenyl)-4,4-dimethyloxazoline in 200 ml of dry tetrahydrofuran is treated dropwise under nitrogen with 50 ml of 2.4 M n-butyllithium in hexane. The solution is stirred at −40° to −30° C. for 45 minutes and a solution of 13.9 g of 4-dimethylaminocyclohexanone in 50 ml of dry tetrahydrofuran is added dropwise, maintaining the temperature at −40° to −30° C. The mixture is stired overnight at −60° to +10° C., diluted with 500 ml of water and extracted with dichloromethane.

The organic phase is washed with water, dried over anhydrous sodium sulfate and concentrated to an oil. The oil is stirred with 50 ml of hexane and 20 ml of ether to yield a material which is recrystallized from ether/hexane (50 ml/50 ml) to provide 26.1% of product, mp 120°–121.5° C.

Analysis: Calculated for $C_{19}H_{28}N_2O_2$: 72.12%C; 8.92%H; 8.85%N. Found: 72.14%C; 8.99%H; 8.94%N.

EXAMPLE 40

3''-Phenyldispiro[1,3-dioxolane-2,1'-cyclohexane-4,1''(3''H)-isobenzofuran]

To a cooled (−50° C.) stirred solution of 27.7 g of 2-bromobenzhydryl methyl ether in 80 ml of dry tetrahydrofuran is added dropwise under nitrogen 60 ml of 2.4 M n-butyllithium in hexane. The mixture is stirred for 2 hours and a solution of 15.9 g of 1,4-dioxaspiro[4.5]decan-8-one in 50 ml of dry tetrahydrofuran is added dropwise, maintaining the temperature at −40° to −30° C. The mixture is stirred overnight at −70° to +10° C., diluted with 100 ml of water and extracted with 100 ml of dichloromethane. The organic phase is washed with water (2×50 ml), dried over anhydrous sodium sulfate and concentrated in vacuo. A solution of the residue in 400 ml of ethanol is stirred with 50 ml of hydrogen bromide/ether at room temperature for 3 hours. The solvent is removed under reduced pressure and the remaining oil crystallizes from 100 ml of methanol to give 39.6% of product, mp 130°–132° C.

Analysis: Calculated for $C_{21}H_{22}O_3$: 78.23%C; 6.88%H; Found: 78.09%C; 6.81%H.

EXAMPLE 41

3'-Phenylspiro[cyclohexane-1,1'(3'H)-isobenzofuran]-4-one

A mixture of 3.22 g of 3''-phenyldispiro[1,3-dioxolane-2,1'-cyclohexane-4',1''(3''H)-isobenzofuran], 350 ml of methanol and 10 ml of 5% hydrochloric acid is stirred at room temperature for 4 hours. The solvent is removed under reduced pressure and the residue crystallizes with 50 ml of water, suction filtered, washed with water and dried. Recrystallization from 200 ml of hexane provides 71.8% of product, mp 143°–145° C.

Analysis: Calculated for $C_{19}H_{18}O_2$: 81.99%C; 6.52%H. Found: 82.21%C; 6.64%H.

EXAMPLE 42

2-[cis-4-(dimethylamino)-1-hydroxycyclohexyl]α-(4-methylphenyl)benzenemethanol

A solution of 3.68 g of 4-dimethylamino-3'-hydroxy-3'-(4-methylphenyl)spiro[cyclohexane-1,1'(3'H)-isobenzofuran] in 50 ml of dry tetrahydrofuran is added dropwise to a suspension of 1.5 g of lithium aluminum hydride in 50 ml of dry tetrahydrofuran and the mixture is stirred at 50°–60° C. for 1.5 hours, cooled to 10° C., hydrolyzed with 50 ml of water and diluted with 100 ml of ether. The organic phase is washed with water (3×50 ml), dried over anhydrous sodium sulfate and concentrated to an oil. The oil is dissolved in 20 ml of ether and diluted with 20 ml of hexane. After cooling overnight (5° C.), the precipitate is collected by filtration to provide 88.6% of product, mp 146°–148° C.

Analysis: Calculated for $C_{22}H_{29}NO_2$: 77.84%C; 8.61%H; 4.13%N. Found: 77.86%C; 8.65% H; 3.90%N.

EXAMPLE 43

2-[cis-4-(dimethylamino)-1-hydroxycyclohexyl]-α-methylbenzenemethanol

A solution of 2.74 g of cis-4-dimethylamino-3'-hydroxy-3'-methylspiro[cyclohexane-1,1'(3'H)-isobenzofuran] in 40 ml of dry tetrahydrofuran is added dropwise to a suspension of 1.5 g of lithium aluminum hydride in 50 ml of dry tetrahydrofuran and the mixture is stirred at 50°–60° C. for 1.5 hours, cooled to 10° C., hydrolyzed with 50 ml of water and diluted with 100 ml of ether. The organic phase is washed with water (3×50 ml), dried over anhydrous sodium sulfate and concentrated to an oil. The oil is dissolved in 10 ml of ether and diluted with 20 ml of hexane. After cooling overnight (5° C.), the crystals are collected by filtration to provide 52.5% of product, mp 147°–148° C.

Analysis: Calculated for $C_{16}H_{25}NO_2$: 72.97%C; 9.57%H; 5.32%N. Found: 73.11%C; 9.66%H; 5.12%N.

EXAMPLE 44 cis-4-(Ethoxycarboxylmethylamino)-3'-phenylspiro[cyclohexane-1,1'(3'H)-isobenzofuran]

To a solution of 15.71 g of cis-4-dimethylamino-3'-phenylspiro[cyclohexane-1,1'(3'H)-isobenzofuran] in 150 ml of dichloromethane is added at 0° C. 10 ml of ethyl chloroformate. The mixture is stirred at room temperature for 1 hour and refluxed overnight. The solvent is removed under reduced pressure and the remaining oil extracted with ether (2×500 ml). The extracts are filtered, the filtrate is made acidic using hydrogen chloride/ether and the solid is collected. The filtrate is washed with water, dried over anhydrous sodium sulfate and concentrated to an oil which is crystallized from 50 ml of hexane to give 26.6% of product, mp 96°–98° C.

Analysis: Calculated for $C_{23}H_{27}NO_3$: 75.59% C; 7.45%H; 3.83%N. Found: 75.84%C; 7.72%H; 3.69%N.

EXAMPLE 45

4-Oximino-3'-phenylspiro[cyclohexane-1,1'(3'H)-isobenzofuran]

A warm solution of 8.35 g of 3'-phenylspiro[cyclohexane-1,1'(3'H)-isobenzofuran]-4-one in 300 ml of ethanol is mixed with a solution of 8.16 g of sodium acetate trihydrate, 4.17 g of hydroxylamine hydrochloride, and 60 ml of water. The solution is refluxed for 120 minutes. The solvent is removed in vacuo and the residue stirred with 300 ml of water. The precipitate is suction filtered, washed with water and dried to give 92.3% of product, mp 172°–175° C.

Analysis: Calculated for $C_{19}H_{19}NO_2$: 77.79%C; 6.53%H; 4.77%N. Found: 77.72%C; 6.45%H; 4.61%N.

EXAMPLE 46

4-Methoximino-3'-phenylspiro[cyclohexane-1,1'(3'H)-isobenzofuran]

A warm solution of 8.35 g of 3'-phenylspiro[cyclohexane-1,1'(3'H)-isobenzofuran-4-one] in one 300 ml of ethanol is mixed with a solution of 8.16 g of sodium acetate trihydrate, 5.01 g of methoxyamine hydrochloride and 80 ml of water. The solution is refluxed for 3 hours. The solvent is removed in vacuo to a total volume of 50 ml and to this mixture is added during 1 hour under stirring, 200 ml of water. The precipitate is suction filtered, washed with water and dried to give 99.6% of product, mp 137°–147° C.

Analysis: Calculated for $C_{20}H_{21}NO_2$: 78.15%C; 6.89%H; 4.56%N. Found: 78.09%C; 6.89%H; 4.28%N.

We claim:

1. A compound of the formula

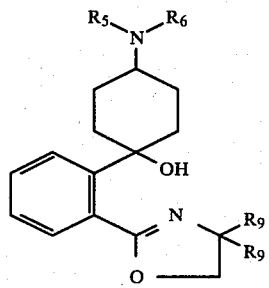

wherein $R_5$, $R_6$ and $R_9$ are loweralkyl; and the geometrical isomers and optical antipodes thereof.

2. The compound of claim 1 which is cis-1-[2-(4,5-dihydro-4,4-dimethyl-2-oxazolyl)phenyl]-4-(dimethylamino)cyclohexanol.

* * * * *

UNITED STATES PATENT AND TRADEMARK OFFICE
CERTIFICATE OF CORRECTION

PATENT NO. : 4,301,292
DATED : November 17, 1981
INVENTOR(S) : Martin, et al.

It is certified that error appears in the above—identified patent and that said Letters Patent is hereby corrected as shown below:

Column 4, line 20: "sodoium" should be --sodium--;

" 6, " 25: "aminioisobenzofuran" should be

--aminoisobenzofuran--;

" 6, " 33: "...aminosiobenzofuran" should be

--...aminoisobenzofuran--;

" 6, " 50: "scheme" should be --Scheme--;

" 13, " 15: "...methoxy -(phenyl..." should be

--...methoxy(phenyl...--

" 13, " 61: "wither" should be --with--;

" 16, " 39: "1.8" should be --1.8 g--;

" 16, " 48: "cl EXAMPLE 11" should be deleted;

" 16, " 49: --EXAMPLE 11-- should be inserted;

UNITED STATES PATENT AND TRADEMARK OFFICE
CERTIFICATE OF CORRECTION

PATENT NO. : 4,301,292

DATED : November 17, 1981

INVENTOR(S) : Martin, et al

It is certified that error appears in the above—identified patent and that said Letters Patent is hereby corrected as shown below:

Column 17, line 7: "...spiro[-cyclohexane..." should be

--...spiro[cyclohexane...--;

" 21, lines "...spiro[-cyclohexane..." should be
5 and 6
--...spiro[cyclohexane...--;

" 22, line 61: "Found:" should be --Found: 78.80%C;

6.95%H; 3.04%N.--;

" 26, " 8: "cis-3'(4-..." should be --cis-3'-(4-...--;

" 26, " 13: "monhydrate" should be --monohydrate--;

" 26, " 19: "anhydrous anhydrous potassium" should be

--anhydrous potassium--;

" 27, " 5: "carbonate" should be --bicarbonate--;

UNITED STATES PATENT AND TRADEMARK OFFICE
CERTIFICATE OF CORRECTION

PATENT NO. : 4,301,292
DATED : November 17, 1981
INVENTOR(S) : Martin, et al

It is certified that error appears in the above—identified patent and that said Letters Patent is hereby corrected as shown below:

Column 27, line 54: "6.44H;" should be --6.44%H--;

" 29, " 29: "4.25N." should be --4.25%N--;

" 29, " 59: "stirrled" should be --stirred--;

" 29, " 67: "stired" should be --stirred--;

" 30, " 50: "...hexyl]α-..." should be --...hexyl] -α-...--;

" 32, " 15: "in one 300 ml" should be --in 300 ml--.

Signed and Sealed this

Ninth Day of March 1982

[SEAL]

Attest:

GERALD J. MOSSINGHOFF

Attesting Officer      Commissioner of Patents and Trademarks